(12) United States Patent
Hirleman, Jr. et al.

(10) Patent No.: US 7,465,560 B2
(45) Date of Patent: Dec. 16, 2008

(54) SYSTEM AND METHOD FOR RAPID DETECTION AND CHARACTERIZATION OF BACTERIAL COLONIES USING FORWARD LIGHT SCATTERING

(75) Inventors: Edwin D. Hirleman, Jr., West Lafayette, IN (US); Songling Guo, Rockville, MD (US); Arun K. Bhunia, West Lafayette, IN (US); Euiwon Bae, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/291,078

(22) Filed: Nov. 30, 2005

(65) Prior Publication Data

US 2006/0172370 A1 Aug. 3, 2006

Related U.S. Application Data

(60) Provisional application No. 60/631,666, filed on Nov. 30, 2004.

(51) Int. Cl.
*C12Q 1/08* (2006.01)
*C12Q 1/06* (2006.01)
*C12Q 1/04* (2006.01)

(52) U.S. Cl. .............................. 435/40; 435/34; 435/39
(58) Field of Classification Search .................. 435/34, 435/39, 40
See application file for complete search history.

(56) References Cited

U.S. PATENT DOCUMENTS

| | | | | |
|---|---|---|---|---|
| 3,892,632 | A * | 7/1975 | Campbell et al. | 435/30 |
| 3,962,040 | A * | 6/1976 | Campbell et al. | 435/287.3 |
| 5,112,745 | A * | 5/1992 | Lorr | 435/38 |
| 5,739,003 | A * | 4/1998 | Brocklehurst et al. | 435/29 |
| 5,863,754 | A | 1/1999 | Bajard | |
| 6,340,570 | B1 | 1/2002 | Anderson et al. | |
| 6,713,019 | B2 * | 3/2004 | Ozasa et al. | 422/82.09 |
| 6,911,312 | B2 | 6/2005 | Anderson et al. | |
| 6,919,960 | B2 | 7/2005 | Hansen et al. | |
| 2005/0048599 | A1 * | 3/2005 | Goldberg et al. | 435/34 |

FOREIGN PATENT DOCUMENTS

| | | |
|---|---|---|
| WO | WO 98/59314 A1 | 12/1998 |
| WO | WO 01/83673 A2 | 11/2001 |
| WO | WO 02/21108 A2 | 3/2002 |
| WO | WO 02/21108 A3 | 3/2002 |

OTHER PUBLICATIONS

Darzynkiewicz Z et al (2000) Analysis of apoptotic cells by flow and laser scanning cytometry. Methods Enzymol, vol. 322, pp. 18-39.*
Wyatt PJ (Mar. 29, 1969) Identification of bacteria by differential light scattering. Nature, vol. 221, pp. 1257-1258.*
Bhunia, A.K. (1998) Antibodies to *Listeria monocytogenes*. *Critical Reviews in Microbiology*. 23: 77-107.
Bhunia, A.K., and Lathrop, A. (2003) Pathogen detection, foodborne. In *McGraw-Hill yearbook of Science and Technology*. New York: McGraw-Hill, pp. 320-323.
Bille, J., Catimel, Bannerman, E., Jacquet, C., Yersin, M.N., Caniaux, I., Monget, D., and Rocourt, J. (1992) API *Listeria*, a new and promising one-day system to identify *Listeria* isolates. *Applied and Environmental Microbiology* 58: 1857-1860.
Bohren, C.F., and Singham, S.B. (1991) Backscattering by nonspherical particles: A review of methods and suggested new approaches. *Journal of Geophysical Research* 96: 52695277.
Dong, Z., Zelmer, C.D., Canny, M.J., McCully, M.E., Luit, B., Pan, B., Faustino, R.S., PIerce, G.N., and Vessey, J.K. (2002) Evidence for protection of nitrogenase from 02 by colony structure in the aerobic diazotroph Gluconacetobacter diazotrophicus. *Microbiology* 148: 2293-2298.
Bronk, B., Druger, S., Czege, J., and Van de Merwe, W. (1995) Measuring diameters of rod-shaped bacteria in vivo with polarized light scattering. *Biophys. J.* 69: 1170-1177.
Buchrieser, C., Rusniok, C., Kunst, F., Cossart, P., and Glaser, P. (2003) Comparison of thegenome sequences of *Listeria monocytogenes* and *Listeria innocua*: clues for evolution and pathogenicity. *Fems Immunology and Medical Microbiology* 35: 207-213.
Francois, P., Bento, M., Vaudaux, P., and Schrenzel, J. (2003) Comparison of fluorescence and resonance light scattering for highly sensitive microarray detection of bacterial pathogens. *Journal of Microbiological Methods* 55: 755-762.
Glaser, P., Frangeul, L., Buchrieser, C. et al. (2001) Comparative Genomics of *Listeria* Species. *Science* 294: 849-852.
Hitchins, A.D. 1995. *Listeria monocytogenes*. In bacteriological Analytical Manual, 8th ed AOAC International, Arlington, VA, pp. 10.01-10.13.
Hu, M. K. (1962). "Visual pattern recognition by moment invariants." *IRE Trans. Inform. Theory* IT 8: 179-187.
Jaradat, Z.W., Schutze, G.E., and Bhunia, A.K. (2002) Genetic homogeneity among *Listeria monocytogenes* strains from infected patients and meat products from two geographic locations determined by phenotyping, ribotyping and PCR analysis of virulence genes. *International Journal of Food Microbiology* 76: 1-10.
Jones, D.D. et al., (1994) Detection of foodborne microbial pathogens. In: *PCR Technology: Current Innovations* p. 341.
Leonard, P., Hearty, S., Brennan, J., Dunne, L., Quinn, J., Chakraborty, T., and O'Kennedy, R. (2003) Advances in biosensors for detection of pathogens in food and water. *Enzyme and Microbial Technology* 32: 3-13.

(Continued)

Primary Examiner—Herbert J Lilling
(74) Attorney, Agent, or Firm—Brinks Hofer Gilson & Lione (57) ABSTRACT

A system and a method of detecting and characterizing a bacterial colony are presented in which the results are determined within about 48 hours. The bacterial colony is disposed on a substrate and placed between a laser and detector. Light from the laser impinges upon and is scattered by the bacterial colony. The forward scattered light is detected by an optical detector. The signal from the optical detector is analyzed by an analyzer and displayed or supplied to a storage medium for review. As different strains of bacteria possess unique forward scattering fingerprints, the particular strain may be identified.

29 Claims, 6 Drawing Sheets

OTHER PUBLICATIONS

Liswith, M.L., Bawolek, E.J., and Hirleman, E.D. (1996) Modeling of light scattering by submicrometer spherical particles on silicon and oxidized silicon surfaces. *Optical Engineering* 35: 858-869.

Nebeker, B.M., de la Pena, J.L., and Hirleman, E.D. (2001) Comparisons of the discretedipole approximation and modified double interaction model methods to predict light scattering from small features on surfaces. *Journal of Quantitative Spectroscopy & Radiative Transfer* 70: 749-759.

Nourrit, V., de Bougrenet de la Tocnaye, J.-L., and Chanclou, P. (2001) Propagation and diffraction of Gaussian beams. *Journal of Optical Society of America A*, 18: 546-556.

Perkins, E.A., and Squirrell, D.J. (2000) Development of instrumentation to allow the detection of microorganisms using light scattering in combination with surface plasmon resonance. *Biosensors & Bioelectronics* 14: 853-859.

Peruski, L. and Peruski, A. H. (2003.). "Rapid diagnostic assays in the genomic biology era: detection and identification of infectious disease and biological weapon agents." *Botechniques* 35: 840-846.

Pine, L., Malcom, G.B., Brooks, J.B., and Daneshvar, M.I. (1989) Physiological studies on the growth and utilization of sugars by *Listeria* species. *Canadian Journal of Microbiology* 35: 245-254.

Salzman, G.C., Griffith, J.K., and Gregg, C.T., (1982) Rapid identification of microorganisms by circular-intensity differential scattering. *Applied and Environmental Microbiology* 44: 1081-1085.

Schmehl, R., Nebeker, B.M., and Hirleman, E.D. (1997) Discretedipole approximation for scattering by features on surfaces by means of a two-dimensional fast Fourier transform technique. *Journal of the Optical Society of America a-Optics Image Science and Vision* 14: 3026-3036.

Suhling M, A. M., Hunziker P, Unser M. (2004). Multiresolution moment filters: theory and applications. *IEEE Trans Image Process.* 13(4):484-95.

Stüll, V.R. (1972) Size Distribution of bacterial cells. *Journal of Bacteriology* 109: 13011303.

Swaminathan, B., and Feng, P. (1994) Rapid Detection of Food-Borne Pathogenic Bacteria. *Annual Review of Microbiology* 48: 401-426.

Teague, M. R. (1980). Image analysis via the general theory of moments. *J. Optical Society of America* 70 (8): 920-930.

Vandemerwe, W.P., Huffman, DR., and Bronk, B.V. (1989) Reproducibility and Sensitivity of Polarized-Light Scattering for Identifying Bacterial Suspensions. *Applied Optics* 28: 5052-5057.

VandeMerwe, W.P., Li, Z.Z., Bronk, B.V., and Czege, J. (1997) Polarized light scattering for rapid observation of bacterial size changes. *Biophysical Journal* 73: 500-506.

Vazquez-Boland, J.A., Kuhn, M., Berche, P., Chakraborty, T., Dominguez-Bernal, G., Goebel, W., Gonzalez-Zorn, B., Wehland, J., and Kreft, J. (201) *Listeria* pathogenesis and molecular virulence determinants. *Clinical Microbiology Reviews* 14: 584-640.

Volokhov, D., Rasooly, A., Chumakov, K., and Chizhikov, V. (2002) Identification of *Listeria* Species by Microarray-Based Assay. *J. Clin. Microbiol.* 40: 4720-4728.

Waltham, C., Boyle, J., Ramey, B., and Smit, J. (1994) Light-Scattering and Absorption Caused by Bacterial-Activity in Water. *Applied Optics* 33: 7536-7540.

Warner, T.L., and Hirleman, E.D. (1997) Toward classification of particle properties using light scattering techniques. *Journal of the Institute of Environmental Sciences* 40: 15-21.

Wyatt, P.J. (1969) Identification of bacteria by differential light scattering. *Nature* 221: 1257-1258.

\* cited by examiner

SYSTEM AND METHOD FOR RAPID DETECTION AND CHARACTERIZATION OF BACTERIAL COLONIES USING FORWARD LIGHT SCATTERING

This application claims the benefit of U.S. Provisional Application No. 60/631,666, filed Nov. 30, 2004.

FEDERALLY SPONSORED RESEARCH OR DEVELOPMENT

This invention was made with Government support under Contract 1935-42000-035 awarded by the United States Department of Agriculture (USDA). The Government may have certain rights in the invention.

BACKGROUND

1. Technical Field

This invention relates to bacterial colonies, and more particularly, to a system and method of detecting and characterizing bacterial colonies.

2. Background Information

Pathogenic bacterial contamination in products not only put the public at risk, but also is costly to companies because of routine product testing, product recalls and liabilities. For example, *Listeria monocytogenes* is one of the major food-borne pathogens with the highest mortality rate (20-28%) among the food pathogens. Traditional methods for detection and identification of bacterial contaminants, such as *Listeria monocytogenes*, typically require 3-7 days and use biochemical or antibody or nucleic acid based tests.

Nucleic acid or antibody-based methods have been successful and are used for pathogen detection by some large food manufactures and regulatory agencies. However, the ability of these methods to differentiate live from dead bacteria and specificity of different strains of closely related species, such as *Listeria*, are of concern. The most reliable and commonly used method for bacterial detection is the classical culture method where test samples are enriched and plated on agar plates for identification of individual colonies by biochemical or serological assays. The assays for identification of the bacterial colonies require multiple steps, and/or use sophisticated and expensive molecular tools requiring a skilled technician to operate the tests.

What is needed is a more rapid, reproducible method and system for detecting and characterizing and identifying bacterial colonies.

BRIEF SUMMARY

By way of introduction only, in one embodiment a system and method of rapid detection and characterization of bacteria growing in colonies using forward light scattering is described. A bacterial colony may be illuminated with a laser beam, and the light scattered in the forward direction by the colony may be detected and analyzed. Automated analysis of the scattering light patterns provides rapid detection and characterization of a variety of strains of *Listeria, Escherichia coli*, and other bacteria and microorganisms.

It is to be understood that both the foregoing general description and the following detailed description of the present invention are merely exemplary and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention.

DETAILED DESCRIPTION

A method and system are described that allow rapid detection of, and differentiation between, various species and strains of bacteria and other microorganisms using non-invasive and non-destructive techniques. These techniques may be used to monitor bacterial pathogens collected from samples of food, water, or air.

Figure 6:
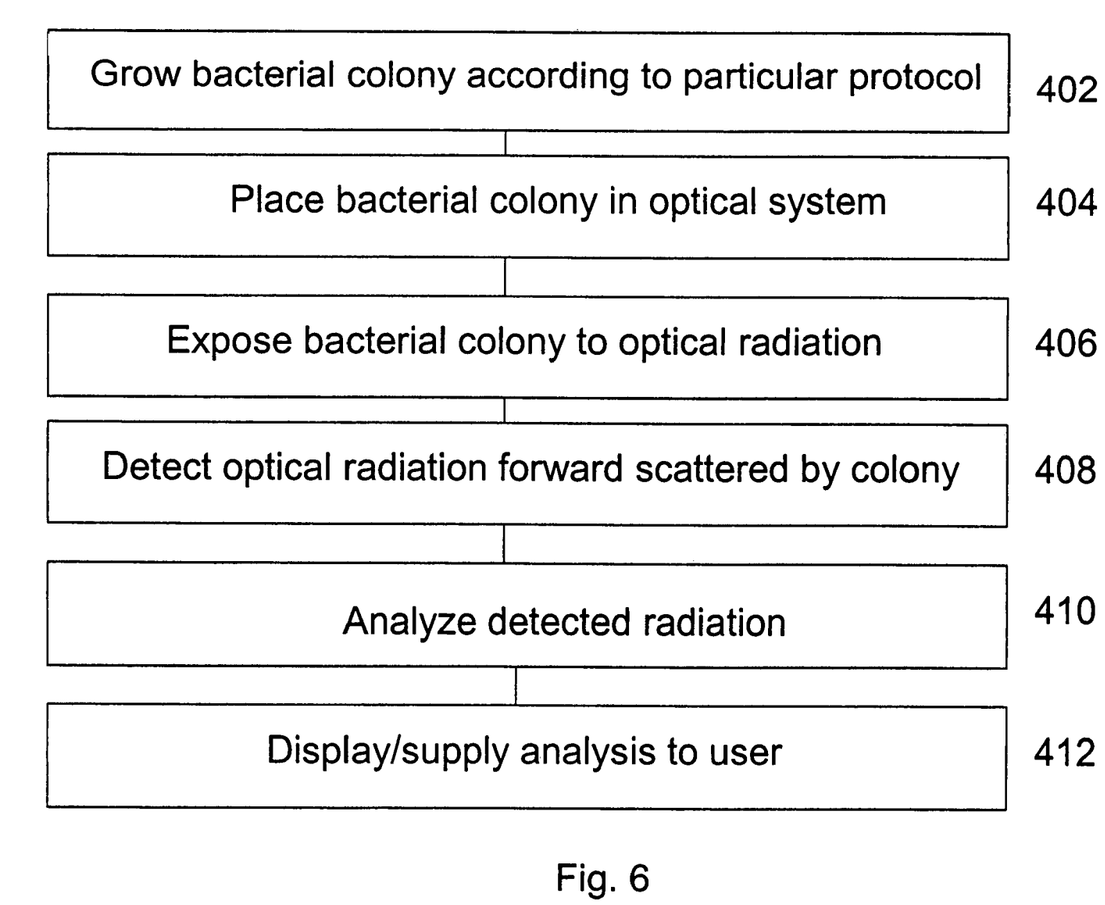
FIG. 6 is a flowchart of one embodiment.

In the method, as shown in FIG. 6, a bacterial colony may be grown according to a protocol 402. The bacterial colony may be disposed in an optical system 404 and exposed to radiation in the optical wavelength regime (about 400 to 800 nm) 406. The forward scattered light may be detected by a detector 408. The pattern and intensity of the forward scattered light may be analyzed to provide characterization of the bacterial colony 410. Different strains of bacteria possess unique forward scattering fingerprints. The results may then be displayed or supplied to a storage medium for review and characterization 412.

Figure 1:
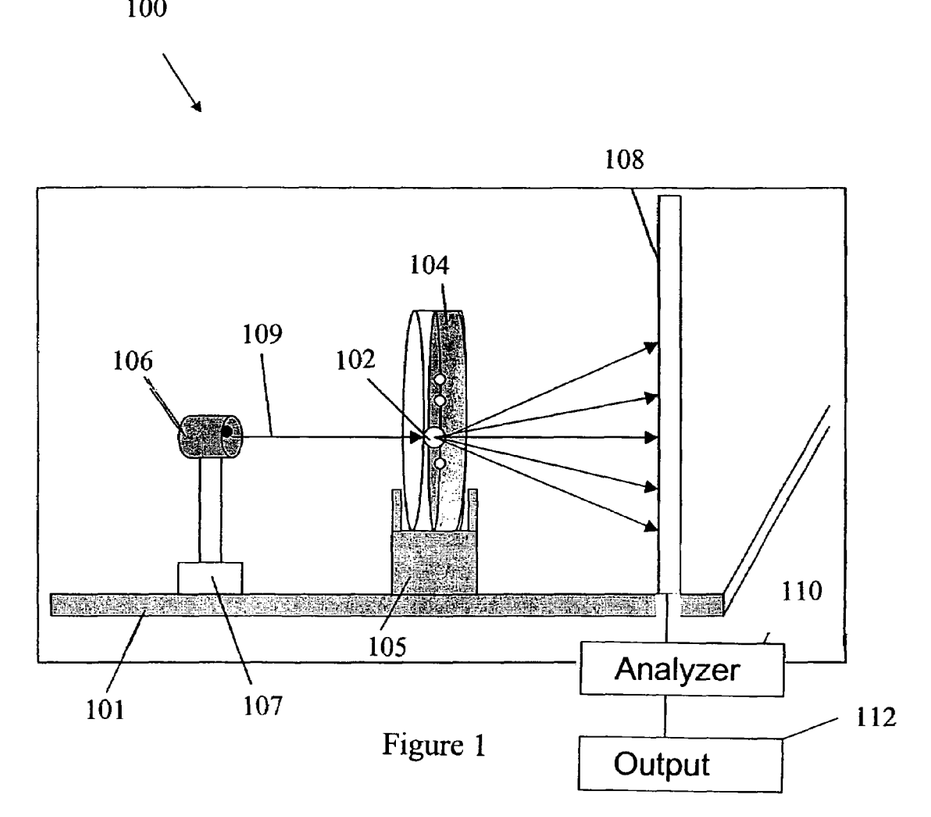
FIG. 1 is a schematic of a system of one embodiment of the present invention.

FIG. 1 illustrates one embodiment of the present system that may be used for characterization of bacterial colonies and other microorganisms. The embodiments and methods described refer to bacterial colonies, however, the present invention may also be used for identification and characterization of other microorganisms and is not limited to only the bacteria or the bacterial examples described below.

In one embodiment of the present invention, a bacterial colony 102 may be grown on a substrate 104 and placed into a system 100 for characterization of the bacterial colony 102 using forward light scatter from the system 100.

As shown in FIG. 1, the system 100 may include a radiation or light source such as a laser 106, a detector 108, an analyzer 110 and an output 112. A sample holder 105 may also be included between the laser 106 and the detector 108. The sample holder 105 may be sized and shaped for holding the substrate 104 in a position for receiving radiation from the laser 106. The substrate 104 may be provided in a Petri dish. The substrate 104 may be solid and include at least one bacterial colony 102. The term "solid" refers to a non-liquid substrate that may be solid or semisolid, for example, an agar plate. The sample holder 105 may be placed in the system 100 such that light from the laser 106 impinges upon the bacterial colony 102 on the substrate 104 in the sample holder 105. The light from the laser 106 that has impinged on the bacterial colony 102 and is scattered in the forward direction may be detected by the optical detector 108. The signal from the optical detector 108 may be analyzed by an analyzer 110 and supplied to an output 112.

The system 100, as shown in FIG. 1, may be built on an optical board 101 to place each component of the system 100 in the desired position and for controlling moving parts. Additionally, the board 101 may provide vibration isolation. In one embodiment of the present invention, the system 100 may include the laser 106, such as a laser diode having a wavelength of about 635 nm, and an x-z moving stage group 107 for holding and moving the laser 106 or the sample holder 105, the substrate 104 and the colony 102. The system 100 may be configured such that the laser 106, the sample holder 105, the detector 108 may be located on an optical path 109 of the laser, in that order. In some embodiments, the distance from the laser 106 to the sample holder 105 may be about 100 mm and the distance from the sample holder 105 to the detector 108 may be about 280 mm. One of skill in the art will recognize that additional distances between the components of the system 100 may be used within the scope of the present invention.

In operation, the bacterial colony 102 and substrate 104 may be placed in the sample holder 105 between the laser 106 and the detector 108. The laser 106 may generate a collimated beam of light in the order of 1 mm diameter (at the $1/e^2$ irradiance points) that may be directed through the center of the bacterial colony 102 and through the substrate 104. One of skill in the art will recognize that additional illumination sources and laser beam diameters at the colony 102 may be used within the scope of the present invention, as long as a sufficient portion of the colony 102 is illuminated and that the detector receives forward scattered radiation of a sufficient intensity to be detected. Optical elements such as lenses may be present in the optical path between the laser 106 and the detector 108, but are not shown for convenience. The laser may emit light of any wavelength, optical, infrared or ultraviolet, so long as the properties of the bacteria colony are not substantially altered by the exposure.

Some of that light from the laser 106 may be reflected from the various interfaces (e.g. substrate, bacteria colony) and some may be absorbed by the colony 102. A fraction of the light may be transmitted unscattered through the substrate 104 and through the bacterial colony 102. Some fraction of the incident light may be scattered in various directions by the bacterial colony 102, and a fraction of that total scattered light may proceed in the forward direction at relatively small angles to the transmitted light. The forward scattered light in a scattering cone of approximately 30 degrees may be detected using the detector 108. The laser 106 or the sample holder 105 and the bacteria colony 102 may be held by the x-z moving stage group 107 that may enable every point of the bacterial colony 102 to be illuminated by the laser 106. One of skill in the art will recognize that sample holder 105 could be held stationary and other optical components moved to sample every point of the colony within the scope of the present invention. The detector 108 may be located at the same y-position as the sample holder 105. The detector 108 may be film or an electronic imaging device such as a CCD Camera or other array of photodetectors. The results may take a relatively short time to determine, generally less than 48 hours. The signals from the detector 108 may be provided to an analyzer 110, such as a computer, and then to an output 112. The analyzer 110 may use an algorithm to determine known samples from the scattering pattern or a model for determining the particular sample if an unknown scattering signature results. The output 112 may be a display or printer or other storage medium. The system may be automated in a turn-key like system such that, for example, a user simply places a sample in a particular location and the system moves the sample, exposes the sample, analyzes the scattering, and tabulates, displays, or provides the results to the user without the need for manual intervention.

Figure 2:
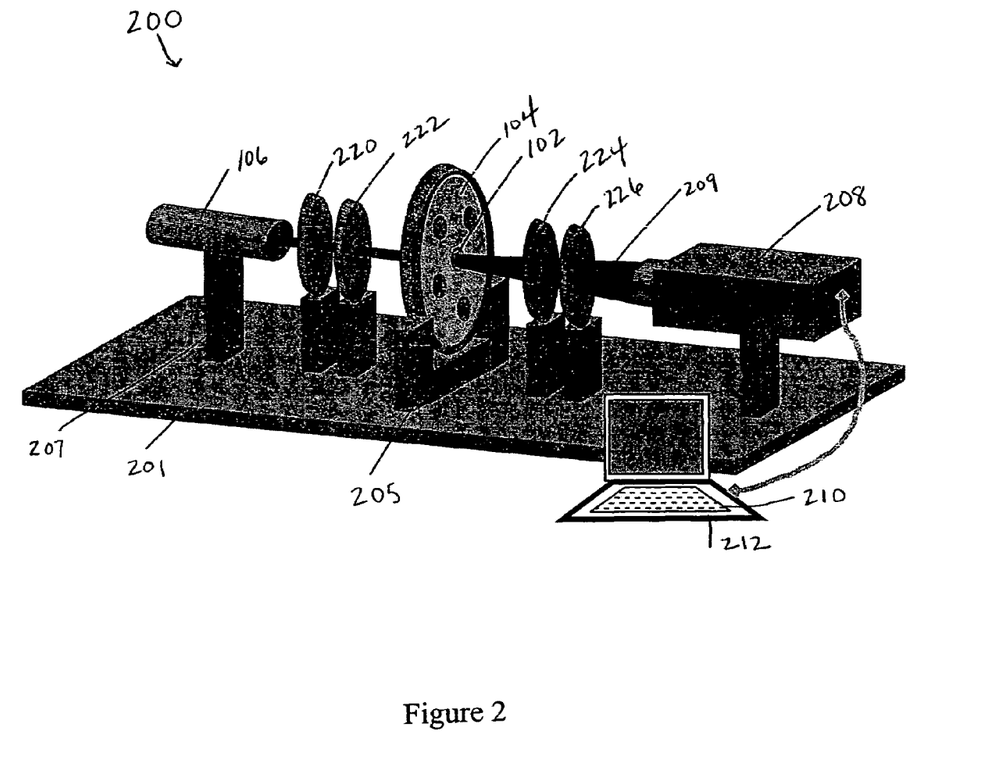
FIG. 2 is a schematic of a system of another embodiment of the present invention.

FIG. 2 illustrates another embodiment of the present invention. A system 200 may include components similar to the system 100 described above including a laser 206, a holder 205, and a detector 208 mounted on an optical board 201, and an analyzer 210 and an output 212. The system may also include additional components such as a liner polarizer (POL) 220, a quarter wave plate (QWP) 222, and a polarization analyzer (ANAL) 226. The detector 208 may be a CCD camera, such as an Alta U260, having a Kodak KAF-0261E interface, Apogee Instruments, Inc. Auburn, Calif. An exemplary system 200 is shown in FIG. 2 where the following components may be aligned along the laser path 209, a laser 206, a POL 220, a QWP 222, a sample holder 205 shown with a bacterial colony 102 on a substrate 104 aligned in the holder 205, a QWP 224, an ANAL 226 and a detector 208. An analyzer 210 and an output 212 may also be included. Using the embodiment shown in FIG. 2, including the POL 220, QWP 222, QWP 224, ANAL 226 and where the detector 208 is a CCD camera, 16 elements of Mueller matrix measurement may be possible. The 16 elements may be used to increase the sensitivity of the images produced and may further be used with image analysis software. The matrix is described in more detail below in Example 3. For a discussion of the Mueller matrix, see W. P. Van De Merwe, D. R. Huffman, and B. V. Bronk, Reproducibility and sensitivity of polarized light scattering for identifying bacterial suspensions, Applied Optics, Vol. 28, No. 23, (1989); C. F. Bohren, D. R. Huffman, Absorption and Scattering of Light by Small Particles, (Wiley, New York, 1983).

Figure 3:
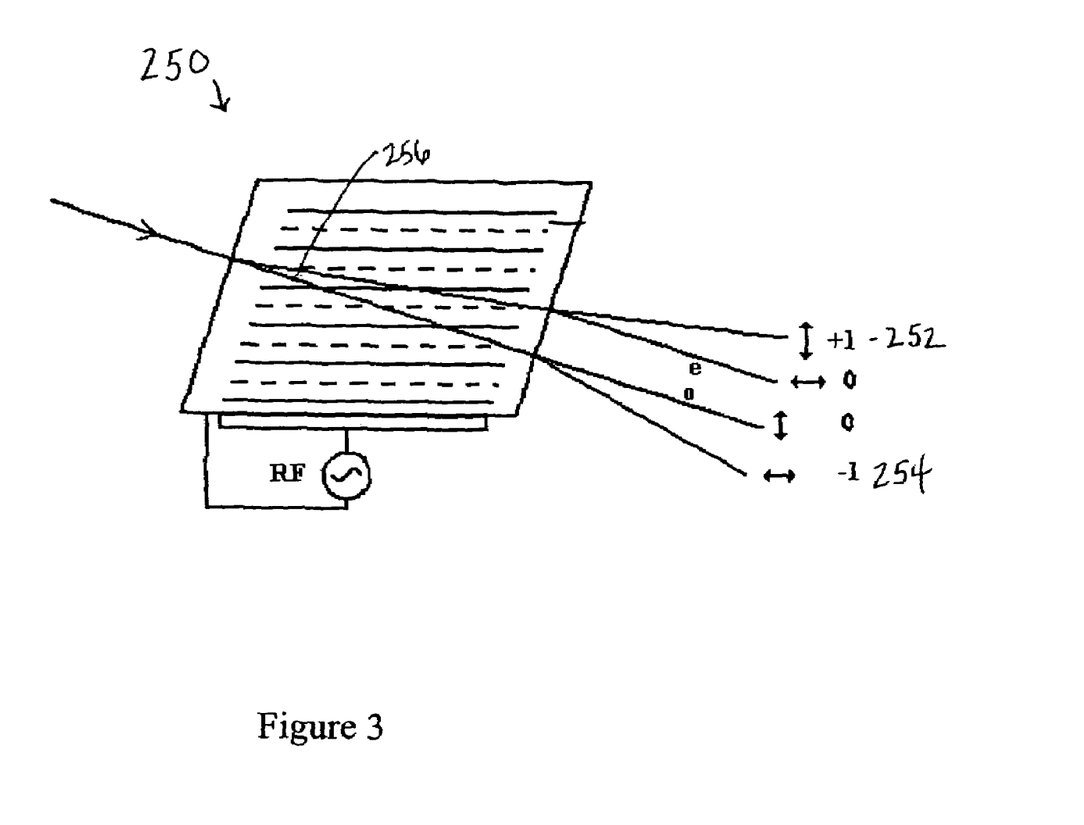
FIG. 3 is a schematic of a filter that may be used with the present invention.

The polarization analyzer 226 may be a simple polarization filter that passes only one linear polarization and may be rotated to measure various Mueller matrix elements. The polarization analyzer 226 may also be an electrically-switched analyzer such as an acoustic optic tunable filter (AOTF)-based polarimetric filter 250, shown in FIG. 3. The AOTF is based on the acoustic diffraction of light in an anisotropic medium. In that case, the polarization analyzer 226 may include a piezoelectric tranducer bonded to a birefringent crystal. When the transducer is excited by an applied RF signal, acoustic waves may be generated in the medium. The propagating acoustic wave may produce a periodic modulation of the index of portions of an incident light beam, in the case of forward scattered light. For a fixed acoustic frequency, a limited band of optical wavelength may satisfy the phase-matching condition and be cumulatively diffracted. As the RF frequency is changed, the center wavelength of the optical pass band may be changed accordingly so that the phase matching condition may be maintained. In some embodiments the crystal material may be $TeO_2$. As shown in FIG. 3, the diffracted light intensity may be directed into two physically separated first order beams, the +1 beam 252 and the −1 beam 254. The angle 256 between the beams 252, 254 may be affected by the system 200 design and typically may be a few degrees. The beams 252, 254 may be orthogonally polarized. When the incident beam from the laser 106, 206 is unpolarized, the beams 252, 254 may have nearly equal power. For polarimetric imaging, the beams 252, 254 may be projected onto two separate detectors 108, 208, such as a camera, or two different areas of the same detector 108, 208.

The bacterial colony 102 for use in the system 100 may be grown on the substrate 104 using protocols known by one of skill in the art. The growth conditions and the substrate may vary, depending on the strain of the bacteria or other microorganism. The following list of bacterial species may be used in the system 100, 200 described above: Gram-positive food-borne bacterial species including, but not limited to, *Listeria, Staphylococcus aureus, Bacillus* spp, *Streptococcus, Carnobacterium, Lactobacillus, Leuconostoc, Micrococcus, Brocothrix* and *Enterococcus*; Gram-negative bacteria including, but not limited to, *Salmonella, E. coli, Yersinia entercolitica, Serratia, Proteus, Aeromonas hydrophilia, Shigella* spp and *Cirobacter freunddi*.

In one aspect of the present invention, the bacterial colony 102 may be grown until the diameter of the colony 102 is approximately 1 to 2 mm when the diameter of the laser beam on the colony 102 may also be about 1 to 2 mm. The diameter of the colony at the time of analysis may be varied, but, preferably, the colony may be grown to a diameter greater than the laser beam. The thickness of the colony (along the optical axis) depends on the species, and may be typically about 0.2 mm to 0.4 mm. The substrate 104 may be a medium which is substantially transparent to the wavelength emitted by the laser 106. For example, the substrate 104 may be an agar substrate, which provides nutrients and an attachment region for the bacteria colony. The substrate 104 with the bacterial colony 102 for analysis, typically in a Petri dish, may be placed in a sample holder 105 of the system 100.

The sample preparation protocol used permits one to obtain repeatable results that allow detection and differentiation of relevant species and strains of bacteria. The bacteria may be grown on agar plates, and incubated for approximately 18 to 36 hours or until the size of the colony reaches a diameter greater than the laser beam to be used. The actual incubation time may vary between genera and species. These samples may be exposed to a laser beam from a laser diode and the results obtained in less than 48 hours.

Figure 4:
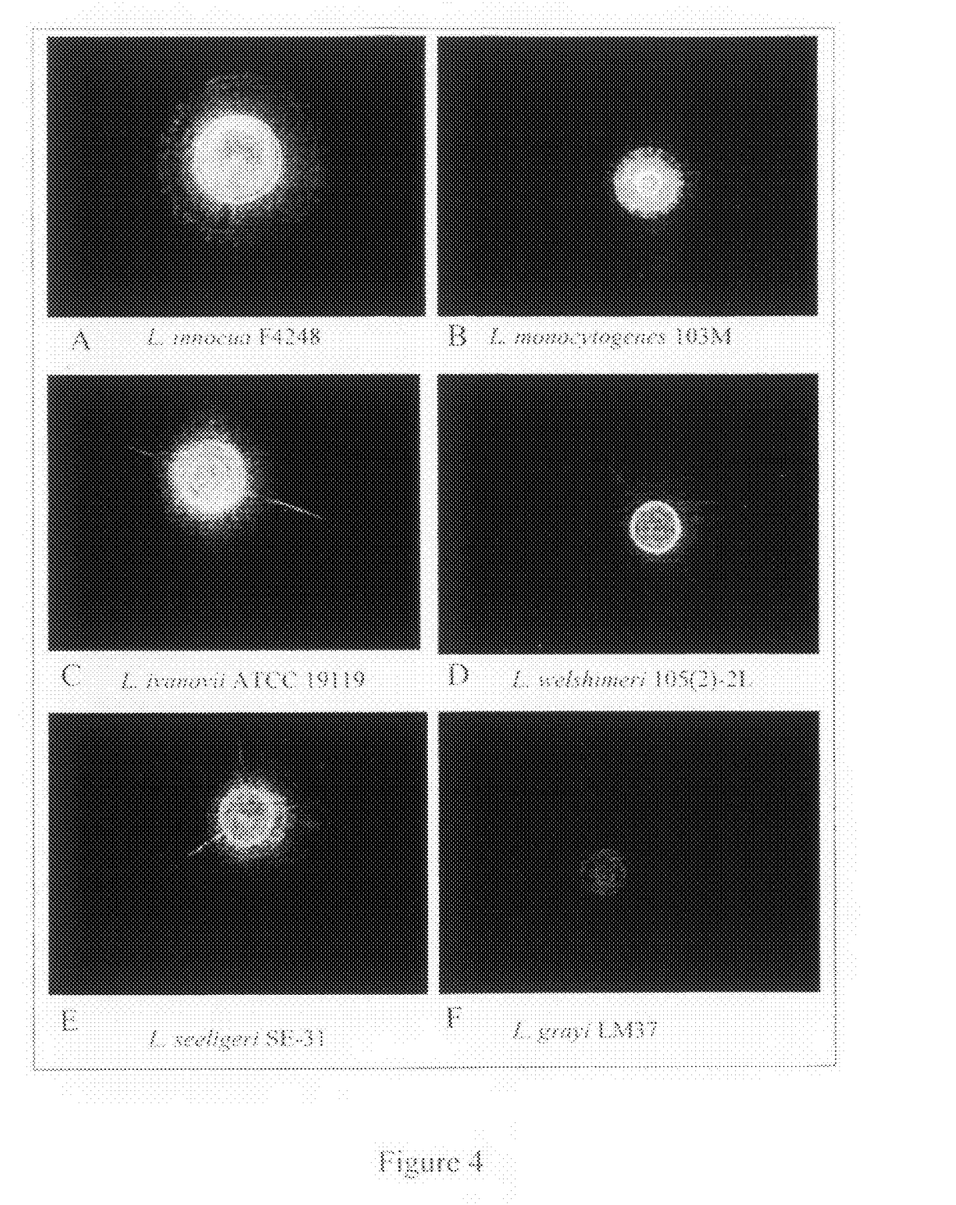
FIG. 4 is a forward scattering pattern from *Listeria* samples (A) *L. innocua*, (B) *L. monocytogenes*, (C) *L. ivanovii*, (D) *L. Welshimeri*, (E) *L. seeligeri*, (F) *L. grayi;*
Figure 5:
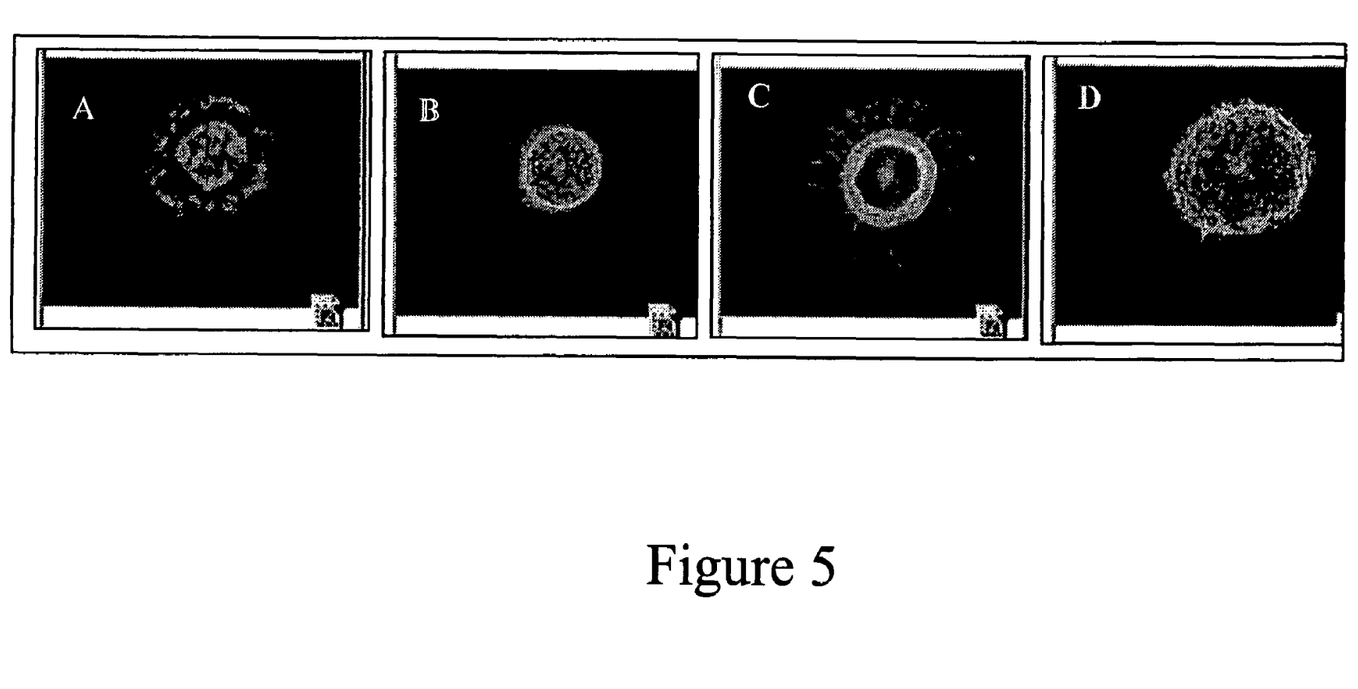
FIG. 5 is a forward scattering pattern from 3 *Listeria* samples and an *E. coli* sample (A) *L. ivanovii*, (B) *L. innocua*, (C) *L. monocytogenes*, and (D) *E. coli*.

Exemplary scatter patterns of several strains of *Listeria* are shown in FIG. 4A-F illustrating the differences in the forward (center of laser beam axis). It is clear that the bacteria used to produce the patterns shown in FIG. 4A-F and FIG. 5A-D generate very different forward scattering patterns. The forward light-scattering different for different species of *Listeria*: e.g. human pathogenic *Listeria monocytogenes* provided a different scattering pattern than non-pathogenic *Listeria*. The repeatability of these patterns for colonies of the same species and strain is very good, and is adequate for classified and differentiation.

One method of characterizing and differentiating bacterial colonies using forward light scattering patterns may be accomplished by assigning certain values to individual unique features in the scattering patterns. In general, the scattering pattern of a bacterial colony may include some radial symmetry, and may be composed of diffraction ring(s). Generally, a spot at the center of the scattering pattern may be included, with size and sharpness varying from strain to strain. Usually at least one ring may be present, and there may be 2, 3, 4 or more rings. The size, thickness, sharpness, and intensity of the ring(s) may also vary from strain to strain. For some strains, there may be diffusion around the innermost ring, and for other strains radial spikes may be present outside of the innermost ring. The integrated intensity of the entire scattering pattern also may vary from stain to strain.

In one embodiment of the present invention, scattering patterns from samples may be scored according to the exemplary features shown in Table I and the samples may be characterized according to the scores. The specific characteristics shown in Table I illustrate one set of scattering pattern features that will allow automated detection and classification of bacteria using forward scattering. One of skill in the art will recognize that additional sets of scattering pattern features and additional approaches of scoring or processing said scattering pattern features may be used within the scope of the present invention.

TABLE I

| Scoring number | Feature | 0 | 1 | 2 | 3 |
|---|---|---|---|---|---|
| A | Central spot existence | No | Yes | | |
| B | Central spot sharpness | N/A | Very sharp | Not sharp | |
| C | Size of central spot | N/A | Large | Small | |
| D | Number of diffraction rings | | | | |
| E | Intensity of first (innermost) ring | N/A | High | Normal | Low |
| F | Size of first ring | N/A | Small | Normal | Large |
| G | Clearness of first ring | N/A | Very Clear | Not clear | |
| H | Thickness of first ring | N/A | Thin | Normal | Thick |
| I | Diffusion around first ring | N/A | Yes | No | |
| J | Average intensity of entire scattering pattern | High | Low | | |
| K | Average intensity of pattern inside first ring, excluding central spot (if applicable) | High | Low | | |
| L | Presence of radial spikes | Not present | Present | | | scatter between *L. innocua*, (B) *L. monocytogenes*, (C) *L. ivanovii*, (D) *L. Welshimeri*, (E) *L. seeligeri*, (F) *L. grayi*. Scatter patterns for several strains of *Listeria* were also compared to a non-pathogenic strain of *E. coli* and the differences in the forward scatter patterns of these strains are shown in FIG. 5A-D. These images were obtained by placing a Petri dish containing bacterial colonies into the system and placing a screen at the detection plane and using a digital camera to record an electronic image of the scattering pattern. The spot in the middle of the scattering pattern is on the optical axis In one embodiment, the features described in Table 1 may be used to characterize and identify different forward light scatter patterns for different bacteria. The results from analysis of bacterial colonies using the attributes from Table I may be stored in a database of known bacterial species for comparison to an unknown sample to characterize and identify the unknown sample. Table II shows the results of the forward light scatter patterns of some of the species tested along with their classification results using the exemplary features shown in Table I. Table II provides an exemplary list of known bacterial species for comparison to an unknown bacterial sample that may be subjected to forward light scatter in the system 100, 200 and characterized and identified based on the forward light scatter pattern. 70 additional strains of bacteria have been analyzed in the system 100 for forward light scatter patterns and the attributes listed in Table I recorded for each strain.

where each colony was subjected to a laser diode having a wavelength of 635 nm and the forward light scatter was detected on a detector. The forward light scatter pattern was collected and analyzed according to the attributes shown in Table I above. The light scattering patterns of *L. innocua*, (B) *L. monocytogenes*, (C) *L. ivanovii*, (D) *L. Welshimeri*, (E) *L. seeligeri*, (F) *L. grayi* are shown in FIG. 4A-F.

TABLE II

|  | A | B | C | D | E | F | G | H | I | J | K | L |
|---|---|---|---|---|---|---|---|---|---|---|---|---|
| *L innocua* F4247 | 0 | 0 | 0 | 1 | 1 | 2 | 1 | 1 | 2 | 0 | 0 | 0 |
| *L innocua* F4248 | 1 | 1 | 1 | 2 | 2 | 1 | 3 | 2 | 0 | 0 | 0 | 0 |
| *L ivanovii* 11919 | 1 | 2 | 1 | 2 | 2 | 1 | 1 | 2 | 2 | 0 | 0 | 0 |
| *L ivanovii* SE98 | 1 | 2 | 1 | 1 | 1 | 2 | 1 | 1 | 2 | 0 | 1 | 0 |
| *L seeligeri* SE31 | 0 | 0 | 0 | 1 | 1 | 1 | 1 | 1 | 2 | 1 | 1 | 0 |
| *L seeligeri* V13 | 1 | 1 | 1 | 2 | 2 | 2 | 1 | 1 | 2 | 1 | 1 | 0 |
| *L grayi* ATCC19120 | 0 | 0 | 0 | 2 | 1 | 2 | 1 | 1 | 2 | 0 | 0 | 0 |
| *L grayi* Lm37 | 1 | 2 | 2 | 2 | 3 | 1 | 1 | 1 | 2 | 1 | 1 | 0 |
| *L welshimeri* 105(2)-2L | 0 | 0 | 0 | 1 | 1 | 2 | 1 | 1 | 2 | 0 | 0 | 0 |
| *L welshimeri* ATCC35897 | 0 | 0 | 0 | 1 | 1 | 1 | 1 | 1 | 2 | 0 | 0 | 0 |
| *L monocytogenes* 101M | 0 | 0 | 0 | 2 | 1 | 1 | 1 | 3 | 2 | 0 | 0 | 0 |
| *L monocytogenes* 103M | 1 | 2 | 1 | 2 | 1 | 1 | 1 | 1 | 2 | 0 | 0 | 0 |

EXAMPLES

Example 1

Colony Culture Conditions

The bacterial cultures listed in the tables were obtained from a frozen glycerol stock (−80° C.) from a collection at Purdue University. The bacteria were grown in brain heart infusion broth (BHI) (Difco, available from Becton Dickinson and Company, Franklin Lakes, N.J.) for 18-24 h at 37° C. The cultures were propagated twice in BHI overnight at 37° C. at 140 rpm in a shaker incubator (New Brunswick Scientific, Edison, N.J.). For individual colony growth, BHI broth supplemented with 1.5% agar (Difco) in Petri dishes was used.

Bacterial plates for light scattering experiments were prepared from cultures grown in BHI. The cultures were serially diluted in sterile 20 mM phosphate buffered saline, pH 7.4 (PBS) so that the dilutions when plated would produce about 30-50 colonies per plate. The diluents were evenly distributed on the surface of BHI agar plates, in duplicate, using a bent glass spreader and were incubated at 37° C. for 18-36 h in a humidified plastic container or until the size of the colony reached about 1.8 to 1.9 mm in diameter. Typically, the thickness of the colony may be about 0.2 to 0.4 mm. Once the colonies reached the preferred diameter, the plates were used in the system. The plates having the colonies of the preferred diameter may also be stored at 4° C. until used in the system. Colony-free areas of the agar plates were examined for uniformity of the agar distribution in the plates prior to using the plates in the system. Confirmation of the identity of the bacterial colonies may be determined by methods known to one of skill in the art, for example by ribotyping in an automated Riboprinter (Qualicon, Willmington, Del.) (Jaradat et al., 2002, *International Journal of Food Microbiology*, 76: 1-10).

Example 2

Comparison of *Listeria* Colony Characteristics

Several strains of *Listeria* were cultured according to the protocol described above and were placed in the system 100

Results of the analysis showed the following: The scattering pattern of *L. innocua* showed a clear central spot, isotropic background, and clear rings. The ring is relatively thick and diffuse, and the average intensity of the whole pattern appears to be high. The scattering pattern of *L. monocytogenes* indicated the presence of a diffused central spot with rings. The innermost ring is small and generally has no diffusion around it. The average intensity of the pattern is high. In *L. ivanovii*, the scatter pattern showed a sharp central spot and some ring characteristics. The average intensity of the whole pattern is high. In the scattering pattern of *L. welshimeri*, there is no central spot and one large ring with minimal diffused scatter around it. In *L. seeligeri*, there is a central spot, but that feature is not very clear. It has one large ring with diffused edges, and the average intensity of the whole pattern is high. The scattering pattern of *L. grayi* had a central spot with 2 rings, and the small innermost ring is sharp and with diffusive scatter around it. The average intensity of the whole pattern is low.

Example 3

Mueller Matrix Characterization

As discussed above for the embodiment shown in FIG. 2, the full 16 elements of Mueller matrix measurement are possible to determine. The Mueller matrix shown below will be used to determine additional characteristics of the stains of bacteria analyzed in the system 200. The Mueller matrix is a 4×4 matrix, which relates incident stokes parameter $S_{i0}$-$S_{i3}$ and scattered stokes parameter $S_{s0}$-$S_{s3}$.

$$\begin{pmatrix} S_{s0} \\ S_{s1} \\ S_{s2} \\ S_{s3} \end{pmatrix} = \begin{pmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{pmatrix} \begin{pmatrix} S_{S10} \\ S_{S11} \\ S_{S12} \\ S_{S13} \end{pmatrix}$$

The matrix will be used to describe the polarization properties of scattered field with given incident field. Conversely, if the input and scattered stokes parameters are measured, the characteristic information of the objects may be extracted. Performing this measurement in two dimensional area, polarization characteristics of the bacterial colony will be obtained. In the embodiment shown in FIG. 1, the single intensity measurement of linearly polarized light is used which is the $M_{12}$ element of the 4×4 matrix. By using the rest of the Mueller matrix element, it will be possible to increase the capability of differentiation of species, to determine the Mueller matrix element that provides the most sensitivity, and the dependency of the Mueller matrix elements to types of species.

Example 4

Growth of Colonies on Selective Media

Growth of the colonies of the different strains of bacteria will be examined to use selective agents in the media used to form the agar plates to eliminate background populations. (See Hitchins et al., 1995, *Listeria moncytogenes*. In Bacteriological Analytical Manual, 8$^{th}$ ed. AOAC International, Arlington, Va., 10.01-10.13.) The thickness of the substrate 104 will generally be about ½" or about 25 ml on a 100 mm diameter Petri dish. Colonies will be grown on different types of media for use in the system 100, 200. Media that will be used include Brain Heart Infusion (BHI) agar, Plate Count Agar (PCA), Tryptic Soy agar (TSA), Luria-Bertini (LB) Agar and Nutrient agar (NA).

Bacterial colonies grown from pigmented bacteria like *Staphylococcus aureus, Serratia* spp and *Micrococcus roseus* will be grown on different media and analyzed in the system 100, 200 to determine the effect of pigmentation on the light scattering properties.

The scatter patterns of spreading bacteria such as *Bacillus* and *Proteus* will also be analyzed in the system 100, 200. Factors that will be examined include controlling the size of the colony and increasing the size of the laser beam.

Example 5

Characterization of Colonies from Naturally or Deliberately Contaminated Food Samples Bacterial colonies grown from naturally or deliberately contaminated food samples will be tested in the system 100, 200. Samples of surface swabs, and both processed and semi-processed foods will be briefly (6-12 h) enriched in the appropriate enrichment broth in a pathogen enrichment detection device where interfering particle such as ionic molecules from a sample are removed from a sample (developed at Purdue University) or other growth chamber suitable for enriching bacterial samples known to one of skill in the art Aliquots of particle-free liquid sample will be dispersed on agar plates for colony growth and the colonies will be analyzed in the system 100, 200 and matched with the attributes of known samples of scatter patterns in a database, such as the attributes shown in Table I.

It is therefore intended that the foregoing detailed description be regarded as illustrative rather than limiting, and that it be understood that it is the following claims, including all equivalents, that are intended to define the spirit and scope of this invention.

The invention claimed is:

1. A system for the characterization of a colony of microorganisms comprising:
    a light source;
    a holder adapted to receive a solid substrate having a surface adapted for growth of colonies of microorganisms, the holder positioned such that light from the light source impinges on at least one colony grown on the solid substrate; and
    a film or electronic imaging optical detector disposed to obtain an image of a forward scattered light pattern from the light impinging on the colony.

2. The system of claim 1, wherein the light source is a laser.

3. The system of claim 2, wherein the laser emits light of a visible wavelength.

4. The system of claim 1, wherein the light source emits light at a wavelength of 635 nm.

5. The system of claim 1, wherein the detector is an array of photo detectors.

6. The system of claim 1, further comprising an analyzer that receives signals from the detector.

7. The system of claim 6, further comprising an output that transmits results from the analyzer to a storage medium or a user.

8. The system of claim 1, further comprising a polarizer, a quarter wave plate, or combinations thereof.

9. The system of claim 1, further comprising a filter.

10. The system of claim 1, wherein the light source or the holder is mounted on a movable member.

11. The system of claim 6, wherein the analyzer further comprises a set of known signals for characterizing the signals received from the detector.

12. A method comprising:
    providing at least one colony of microorganisms on a solid substrate;
    providing a radiation path;
    placing the at least one colony in the radiation path;
    detecting radiation that has been forward scattered by the at least one colony;
    obtaining an image of a forward scattered radiation pattern by a film or electronic imaging optical detector; and
    analyzing the image.

13. The method of claim 12, further comprising comparing the image from the detected radiation to a set of known images and characterizing the colony by quantifying at least one feature of the image.

14. The method of claim 12, further comprising transmitting analyzed results to a storage medium or a user.

15. The method of claim 12, further comprising providing a laser beam to provide the radiation path.

16. The method of claim 12, further comprising polarizing the radiation.

17. The method of claim 12, wherein the substrate comprises agar.

18. A method of characterizing a bacterial colony, the method comprising:
    providing a bacterial colony on a solid substrate;
    providing a light source directed to the bacterial colony;
    providing a film or electronic imaging optical detector for receiving forward scattered light from the light source directed through the bacterial colony;
    detecting a forward scattered light pattern on the detector;
    obtaining an image of the forward scattered light pattern;
    analyzing the image of the forward scattered light pattern received on the detector; and
    taxonomically identifying the bacterial colony based on the image.

19. The method of claim 18, wherein the bacterial colony is provided on an agar substrate.

20. A system for the characterization of at least one colony of microorganisms comprising:
    a light source;

a solid substrate having a surface adapted for growth of colonies of microorganisms positioned such that light from the light source is directed to the at least one colony grown on the solid substrate; and a film or electronical imaging optical detector disposed to obtain an image of a forward scattered light pattern from the light source directed to the at least one colony.

21. The system of claim 1, further comprising a scoring system adapted to score the image of the forward scattered light pattern.

22. The system of claim 21, wherein the scoring system comprises a diffraction ring score.

23. The system of claim 21, wherein the scoring system comprises an intensity score.

24. The system of claim 21, wherein the scoring system comprises a central spot score.

25. The system of claim 21, wherein the scoring system comprises a radial pattern score.

26. The method of claim 12, comprising analyzing the image by quantifying at least one feature of the image.

27. The method of claim 12, further comprising taxonomically identifying a bacterial colony using the image.

28. The method of claim 26, comprising quantifying at least one of a diffraction ring score, an intensity score, a central spot score, and a radial pattern score.

29. The method of claim 18, wherein analyzing the image further comprises quantifying a feature of the image and providing a score.

* * * * *

UNITED STATES PATENT AND TRADEMARK OFFICE
CERTIFICATE OF CORRECTION

PATENT NO. : 7,465,560 B2　　　　　　　　　　　　　　　　　　　　　　Page 1 of 1
APPLICATION NO. : 11/291078
DATED : December 16, 2008
INVENTOR(S) : Edwin D. Hirleman, Jr. et al.

It is certified that error appears in the above-identified patent and that said Letters Patent is hereby corrected as shown below:

On the Title Page

Column 2, line 1, delete "(1998)" and substitute --(1997)-- in its place; line 14, delete "Plerce, G.N." and substitute --Pierce, G.N.-- in its place; line 22, delete "thegenome" and substitute --the genome-- in its place.

Page 2, column 1, line 5, under "OTHER PUBLICATIONS", delete "discretedipole" and substitute --discrete-dipole-- in its place.

Page 2, column 2, line 10, after "*Optical Society*" delete "*ofAmerica*" and substitute --*of America*-- in its place.

Signed and Sealed this

Thirtieth Day of June, 2009

JOHN DOLL
*Acting Director of the United States Patent and Trademark Office*